United States Patent [19]

Klose et al.

[11] 4,368,261
[45] Jan. 11, 1983

[54] METHOD AND REAGENT FOR THE DETERMINATION OF TRIGLYCERIDES

[75] Inventors: Sigmar Klose, Berg; Albert Röder, Seeshaupt; Walter Schneider, Weilheim, all of Fed. Rep. of Germany

[73] Assignee: Boehringer Mannheim GmbH, Mannheim-Waldhof, Fed. Rep. of Germany

[21] Appl. No.: 213,702

[22] Filed: Dec. 5, 1980

[30] Foreign Application Priority Data

Dec. 14, 1979 [DE] Fed. Rep. of Germany ....... 2950381

[51] Int. Cl.$^3$ .......................... C12Q 1/48; C12Q 1/44; G01N 31/00; C12Q 1/32
[52] U.S. Cl. ........................................ 435/15; 435/19; 435/26; 435/194; 435/810; 435/832; 424/2; 436/71
[58] Field of Search ..................... 435/15, 19, 26, 188, 435/194, 805, 810; 23/230 B

[56] References Cited

U.S. PATENT DOCUMENTS

| | | | |
|---|---|---|---|
| 3,862,009 | 1/1975 | Wahlefeld et al. | 435/19 |
| 4,229,527 | 10/1980 | Ziegenhorn et al. | 435/19 |
| 4,241,178 | 12/1980 | Esders et al. | 435/13 |
| 4,245,041 | 1/1981 | Denney | 435/13 |
| 4,246,342 | 1/1981 | Misaki et al. | 435/19 |
| 4,259,440 | 3/1981 | Gupta et al. | 435/15 |

FOREIGN PATENT DOCUMENTS 2737287 2/1978 Fed. Rep. of Germany ........ 435/19

OTHER PUBLICATIONS

Comer et al., Purification and Properties of Glycerokinase from *Bacillus Sternothermophilis*–J. Appl. Biochem. 1(3), 1979, pp. 256-270.

Hawley, Condensed Chemical Dictionary 1974, Van Nostrand Reinhold Co., N.Y., pp. 862 and 903.

Atkinson et al., Behavior of *Bacillus Sternothermophilis* Grown in Different Media, J. Appl. Bacteriol., 1975, 38(3), 301–304.

*Primary Examiner*—Thomas G. Wiseman
*Assistant Examiner*—John E. Tarcza
*Attorney, Agent, or Firm*—Felfe & Lynch

[57] ABSTRACT

A method for the determination of triglycerides by ester cleavage utilizing lipase and optionally esterase with the formation of fatty acids and glycerol, phosphorylation of the glycerol with adnosine triphosphate in the presence of glycerol kinase with the formation of glycerol-1-phosphate and adenosine diphosphate and determination of one of the latter two products. The glycerol kinase used is from *Bacillus stearothermophilis* and acts in combination with at least one activator selected from the group consisting of detergents, phenol derivatives and aniline derivative.

28 Claims, No Drawings

METHOD AND REAGENT FOR THE DETERMINATION OF TRIGLYCERIDES

This invention relates to a method and a reagent for the determination of triglycerides. More specifically, the invention relates to such determination involving the splitting of esters by means of lipase and optionally of esterase.

A known process for determining triglycerides in biological material and preferably in serum is based upon the following reaction sequence:

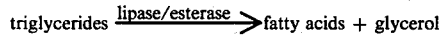

GK = glycerokinase
ATP = adenosine triphosphate
ADP = adenosine diphosphate

It is also known that, the first reaction step according to equation (1), activators must be added which enable the lipase or lipolysis enzymes (in the case of many lipase preparations, the rate of splitting is improved by the addition of esterase) to split the triglycerides at all. In general, surface-active agents are used as activators. However, substituted aryl alcohols, for example dichlorophenol, can also be used together with the surface-active compounds and lead to an even better activation.

However, an important drawback of the activators is the fact that they have a disadvantageous influence on the glycerokinase (E.C. 2.7.1.30) which is required in the second reaction step according to equation (2). This can be seen from the following Table 1 which shows the stability data for a known glycerokinase in the presence and in the absence of stabilizers:

TABLE 1

Stability of glycerokinase from *Candida mycoderma* under the influence of various additives at 25° C.

| additive | residual activity in % after | | | | |
|---|---|---|---|---|---|
| | 0.5 hrs. | 1 hr. | 2 hrs. | 3 hrs. | 4 hrs. |
| none | — | 95 | 92 | 86 | 80 |
| alkyl aryl polyethylene oxide ether | — | 90 | 76 | 67 | 57 |
| taurodesoxycholate | — | 78 | 61 | 40 | 23 |
| 2,3-dichlorophenol | <5 | 0 | 0 | 0 | 0 |

Therefore, it was previously necessary to add the glycerokinase immediately before carrying out the determination. However, there is a significant disadvantage for the reagent because in modern techniques it is desirable to have reagents available which, in a single mixture ready for use, contain all the components with the greatest possible stability. Only under this precondition is it possible to carry out economic working, especially in automatic analyzers.

Because of the instability of glycerokinase in the presence of the mentioned activators for the lipase reaction, the previous procedure was to mix a reagent mixture, without the glycerokinase, with the sample, to allow the blank reaction to run (about 10 minutes), then, after reading off a first extinction, to add the glycerokinase, after the expiry of approximately a further 10 minutes, to determine a second extinction. The triglyceride concentration was then calculated from the extinction difference. The reagent thereby also contained a system for the determination of the ADP formed. However, it would also be possible to measure ADP instead the glycerol-1-phosphate formed.

It is an object of the present invention to find a way, in the case of a process and a reagent for the determination of triglycerides, of improving the stability of glycerokinase in the presence of the abovementioned activating agents such that the necessity is avoided of having to add this enzyme immediately prior to the reaction.

Surprisingly, we have now found that a glycerokinase from *Bacillus stearothermophilis* is stable in the presence of the activators and, therefore, the mentioned disadvantages can be overcome by the use of this enzyme.

Therefore, according to the present invention, there is provided a process for the determination of triglycerides by ester splitting by means of lipase and esterase with the formation of fatty acids and glycerol, phosphorylation of the glycerol with ATP in the presence of glycerokinase with the formation of glycerol-1-phosphate and ADP and determination of one of these two substances formed, wherein there is used a glycerokinase from *Bacillus stearothermophilis* in combination with at least one activator selected from the group consisting of detergents, phenol derivatives and aniline derivatives.

It is known that *Bacillus stearothermophilis* contains a glycerokinase (see J. Appl. Bac., 38, 301–304/1975). However, it could not be deduced from this that this glycerokinase would display a good stability towards the mentioned group of activators which would permit its use together with these activators. This superior stability towards some typical activators, in comparison with glycerokinase from other biological materials, is shown by the activity values set out in the following Table 2:

TABLE 2

Stability of glycerokinase (GK) from various micro-organisms at 25° C.

| source of GK | concentration of dichlorophenol | residual activity after | |
|---|---|---|---|
| | | 30 min. | 60 min. |
| *Candida mycoderma* | 2 mM | 68% | 56% |
| | 5 mM | 18% | 7% |
| *Bacillus stearothermophilis* | 2 mM | 100% | 100% |
| | 5mM | 100% | 100% |
| *Escherichia coli* (commercially available) | 2 mM | 93% | 87% |
| | 5 mM | 81% | 58% |

The activator used according to the present invention is preferably a detergent selected from the group consisting of the polyethylene oxide esters and ethers, the bile acids and the alkyl sulphates, single or in the form of mixtures. From the phenol and aniline group of derivatives, those are preferred as activators which are substituted with a carboxyl group, a sulphonic acid group, one, two or three halogen atoms and/or one or two nitro groups. Chlorine and bromine are the preferred halogen atoms.

Examples of strains of the *Bacillus stearothermophilis* type used for obtaining the enzyme employed according to the present invention include, in addition to the NCIB 8924 (NCA 1503; ATCC 7954) mentioned in the above-cited literature reference, also the mutants NCIB 111270 and 111271 known from Federal Republic of Germany Patent Specification No. 27 38 184. Use can also be made of other strains of *Bacillus stearothermophilis* with a content of glycerokinase which makes working up thereof worthwhile. The biomass is preferably cultured on a glycerol-containing medium, since, in many cases, a higher content of enzyme in the biomass is hereby achieved.

As already mentioned above, in the process according to the present invention, glycerol-1-phosphate or ADP formed according to equation (2) is determined, using methods known for this purpose.

According to a preferred embodiment, ADP is reacted in known manner by phosphorylation with phosphoenolpyruvate in the presence of pyruvate kinase with the formation of ATP and pyruvate. The pyruvate is then oxidized with reduced nicotinamide-adenine dinucleotide (NADH) in the presence of lactate dehydrogenase (LDH) to give nicotinamide-adenine dinucleotide, this latter compound then being measured in the usual way.

Alternatively, in the process of the present invention, glycerol-1-phosphate is reacted with oxygen in known manner in the presence of glycerol-1-phosphate oxidase to give dihydroxyacetone phosphate and hydrogen peroxide, this latter then being reacted with 4-aminoantipyrin and a phenol or aniline derivative in the presence of peroxidase to give a colored material, which is measured.

According to another embodiment of the process of the present invention, ADP is reacted in known manner by phosphorylation with phosphoenol pyruvate in the presence of pyruvate kinase to give ATP and pyruvate, the pyruvate formed is allowed to react with oxygen and pyruvate kinase to give acetyl phosphate, carbon dioxide and hydrogen peroxide and the latter compound is then determined in the above-described manner.

The present invention also provides a reagent for the determination of triglycerides, comprising lipase, esterase, ATP, glycerokinase and a system for determining glycerol-1-phosphate or ATP, wherein the glycerokinase, which has been obtained from *Bacillus stearothermophilis*, is in combination with an activator selected from detergents, phenol derivatives and aniline derivatives.

For the preferred activators in the reagent according to the present invention, there apply equally the above remarks made in connection with the process. Thus, a content of a polyethylene oxide ester or ether, of a bile acid and/or of an alkyl sulphate is preferred. The phenol or aniline derivative used is preferably one which is substituted by a carboxyl group, a sulphonic acid group, one, two or three halogen atoms and/or one or two nitro groups. The halogen atom is preferably bromine or chlorine.

In the case of a preferred embodiment of the reagent according to the present invention, the system for the determination of ADP comprises phosphoenol pyruvate, pyruvate kinase, NADH and lactate dehydrogenase. The activator used is preferably sodium dodecyl phosphate. Another activator combination which is preferred in this connection comprises dichlorophenol, sodium cholate and an alkyl aryl polyethylene oxide ether.

A preferred reagent with this composition contains:
60 to 200 U lipase,
0.4 to 10 U esterase,
0.5 to 10 U glycerokinase from *Bacillus stearothermophilis*,
0.5 to 10 U pyruvate kinase (PK),
2 to 10 U lactate dehydrogenase,
0.25 to 0.7 μMol phosphoenol pyruvate (PEP),
0.25 to 0.7 μMol ATP,
0.15 to 0.3 μMol NADH,
0.3 to 0.5 μMol sodium dodecylsulphate,
4 to 100 μMol magnesium sulphate and
20 to 100 μMol phosphate buffer (pH 6.8 to 7.5) referred to 1 ml. of reagent solution.

Another preferred reagent of this kind contains:
0.6 to 10 U esterase,
60 to 300 U lipase,
0.5 to 10 U glycerokinase from *Bacillus stearothermophilis*,
0.5 to 10 U pyruvate kinase,
2 to 10 U lactate dehydrogenase,
0.15 to 3 μMol NADH,
0.25 to 0.7 μMol phosphoenol pyruvate,
0.25 to 0.7 μMol ATP,
1.5 to 4 μMol 2,3-dichlorophenol,
1.5 to 5.0 mg. sodium cholate,
0.8 to 2 μl. octylphenylpolyethyleneoxide ester (9 to 10 ethoxy units)
150 to 300 μMol magnesium sulphate and
40 to 100 μMol tris/powdered tartaric acid (pH 7.0 to 7.6) referred to 1 ml. of reagent solution.

Another preferred reagent according to the present invention contains, as the system for determining glycerol-1-phosphate, glycerophosphate oxidase, peroxidase and 4-aminoantipyrin. As activator, it preferably contains 2,4-dichlorophenol, together with a cholate and a polyethylene oxide ether and especially preferably isotridecyl polyethylene oxide ether.

An especially preferred composition for a reagent of this type contains:
0.6 to 10 U esterase,
60 to 300 U lipase,
0.5 to 10 U glycerokinase from *Bacillus stearothermophilis*,
2 to 10 U glycerophosphate oxidase,
0.3 to 1 μMol ATP,
3 to 10 μMol 2,4-dichlorophenol,
1.5 to 5.0 mg. sodium cholate,
1.5 to 10 μl. isotridecylpolyethylene oxide ether,
150 to 300 μMol magnesium sulphate and
40 to 100 μMol buffer (pH 7.5 to 8.5) referred to 1 ml. of reagent solution.

The reagent according to the present invention comprises a mixture of all of the components in solid or dissolved form. Because of the great stability of all of its components, it is especially suitable for impregnating solid carrier materials, for example paper, synthetic resin films and the like. Impregnated carrier materials of this kind are especially suitable for rapid tests.

The superior stability of the reagents according to the present invention in comparison with a reagent of the same composition but with a glycerokinase obtained from a different starting material is shown by the following Table 3:

TABLE 3

Comparison of the stability of reagents for the determination of triglycerides with glycerokinase from *Candida mycoderma* and *Bacillus stearothermophilis*

Reagent: phosphate buffer 20 mM (pH 7): 4 mM MgSO4; 0.35 mM sodium dodecyl sulphate; 0.2 mM NADH; 0.44 mM ATP; 0.36 mM PEP; 6 U/ml. LDH; 1 U/ml. PK; 80 U/ml. lipase; 0.6 U/ml. esterase

| standing time in hours | GK (*Cand. myc.*) residual activity in %; 4° C. | GK (*Bac. stearoth.*) residual activity in %; 4° C. |
|---|---|---|
| 0.5 | 5 | 100 |
| 1 | 6 | 100 |
| 5 | 2 | 94 |
| 8 | — | 100 |
| 50 | — | 98 |

Insofar as NADH is formed by the process, it is also possible to convert this, in the presence of an electron carrier, for example diaphorase, phenacine methosulphate or Meldola Blue, with a tetrazolium salt into a colored formazan which can be measured in the usual way for color substances.

In the following Examples, which are given for the purpose of illustrating the present invention, use is made of the following abbreviations:
- ATP = adenosine triphosphate
- ADP = adenosine diphosphate
- PEP = phosphoenol pyruvate
- NADH = nicotinamide-adenine dinucleotide (reduced form)
- NAD = nicotinamide-adenine dinucleotide (oxidized form)
- GK = glycerokinase
- PK = pyruvate kinase
- LDH = lactate dehydrogenase.
- POX = pyruvate oxidase

EXAMPLE 1

Determination of ADP

Reagent 1:
- 20 mM phosphate buffer (pH 7)
- 4 mM MgSO4
- 0.35 mM sodium dodecyl sulphate
- 0.2 mM NADH
- 0.44 mM ATP
- 0.36 mM PEP
- 6 U/ml. LDH
- 1 U/ml. PK
- 80 U/ml. lipase
- 0.6 U/ml. esterase Reagent 2:
identical with Reagent 1+1 U/ml. GK Carrying out of the test:

Into two optically balanced cuvettes (1 cm. optimum path length), 2.5 ml. Reagent 1 are pipetted in cuvette 1 and 2.5 ml. of Reagent 2 in cuvette 2. 0.050 ml. of sample is then pipetted into each cuvette and left to stand for 15 minutes at ambient temperature. The extinction is then read off at 365 nm.

Evaluation:
$(E_1 - E_2) \times 1318 =$ mg. triglyceride/100 ml.

EXAMPLE 2

Determination of ADP

Reagent 1:
- 60 mM tris/tartaric acid buffer (pH 7.3)
- 200 mM MgSO4
- 2 mM 2,3-dichlorophenol
- 1 ml./liter octylphenylpolyethylene oxide ester
- 1.0 g./liter sodium cholate
- 0.44 mM ATP
- 0.36 mM PEP
- 0.2 mM NADH
- 6 U/ml. LDH
- 1 U/ml. PK
- 80 U/ml. lipase
- 1 U/ml. esterase Reagent 2:
identical with Reagent 1+1 U/ml. GK The test and evaluation are carried out in the manner described in Example 1.

EXAMPLE 3

Determination of glycerol-1-phosphate according to the following reaction equations:

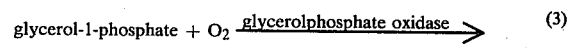

$$\text{glycerol-1-phosphate} + O_2 \xrightarrow{\text{glycerolphosphate oxidase}} \text{dihydroxyacetone} + H_2O_2 \quad (3)$$

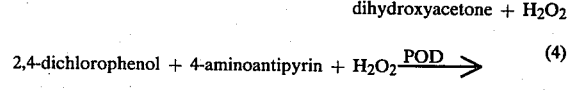

$$2,4\text{-dichlorophenol} + 4\text{-aminoantipyrin} + H_2O_2 \xrightarrow{\text{POD}} \text{quinoid color material} + H_2O \quad (4)$$

Reagent:
- 60 mM tris/tartaric acid buffer (pH 8)
- 200 mM MgSO4
- 5 mM 2,4-dichlorophenol
- 1 ml/liter isotridecyl ether
- 1.7 g./liter sodium cholate
- 0.4 mM ATP
- 3 U/ml. glycerol phosphate oxidase*
- 1 U/ml. GK
- 1 mM 4-aminoantipyrin
- 80 U/ml. lipase
- 1 U/ml. esterase

* see Arch. Biochem. Biophys., 80, 250–255/1960.

Carrying out of the test.

2.0 ml. of reagent and 0.020 ml. sample are pipetted into a cuvette and incubated for 15 minutes at ambient temperature. The extinction is then read off at 500 nm. Evaluation is carried out, after subtraction of a reagent blank value from the measured value, by comparison with a triglyceride standard of known concentration.

EXAMPLE 4

Determination of ADP according to the following reaction equations:

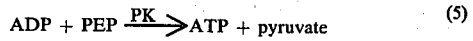

$$\text{ADP} + \text{PEP} \xrightarrow{\text{PK}} \text{ATP} + \text{pyruvate} \quad (5)$$

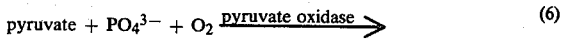

$$\text{pyruvate} + PO_4^{3-} + O_2 \xrightarrow{\text{pyruvate oxidase}} \text{acetyl phosphate} + CO_2 + H_2O \quad (6)$$

(7) same as reaction (4) in Example 3.

Reagent:
- 60 mM tris/tartaric acid buffer (pH 7.3)
- 4 mM MgSO4
- 10 mM 2,4-dichlorophenol
- 1 ml/liter isotridecyl ether
- 1.7 g./liter sodium cholate 0.1 mM ATP
0.1 mM PEP
80 U/liter lipase
1 U/liter esterase
1 U/liter GK
1 U/liter POX
1 U/liter PK Carrying out of the test.

20 μl. of sample and 3 ml. of reagent are incubated for 20 minutes. The extinction is then measured at 500 nm and the extinction of a reagent blank value is subtracted therefrom. By way of a calibration with a standard, the concentration in the unknown sample is calculated from the extinction difference.

It will be understood that the specification and examples are illustrative but not limitative of the present invention and that other embodiments within the spirit and scope of the invention will suggest themselves to those skilled in the art.

What is claimed is:

1. In a method for the determination of triglycerides which comprises combining sample, lipase, glycerol kinase, adenosine triphosphate, and at least one lipase activator selected from the group consisting of polyethylene oxide ester surfactants, polyethylene oxide ether surfactants, bile acid surfactants, alkyl sulphate surfactants, phenol derivatives, and analine derivatives, under conditions suitable to form glycerol-1-phosphate and adenosine diphosphate and determining the presence or concentration of either glycerol-1-phosphate or adenosine diphosphate, the improvement comprising using a glycerol kinase from *Bacillus stereothermophilis*.

2. Method as claimed in claim 1 wherein said activator is a polyethylene oxide ester.

3. Method as claimed in claim 1 wherein said activator is a polyethylene oxide ether.

4. Method as claimed in claim 1 wherein said activator is a bile acid.

5. Method as claimed in claim 1 wherein said activator is an alkyl sulphate.

6. Method as claimed in claim 1 wherein said activator is a phenol substituted with a substituent selected from the group consisting of carboxyl, sulphonic, halogen and nitro.

7. Method as claimed in claim 1 wherein said activator is an aniline substituted with a substituent selected from the group consisting of carboxyl, sulphonic, halogen and nitro.

8. Method as claimed in claim 1 wherein said *Bacillus stearothermophilis* is *Bacillus stearothermophilis* NCIB 8924.

9. Method as claimed in claim 1 wherein said adenosine diphosphate is phosphorylated with phosphoenol pyruvate in the presence of pyruvate kinase with the formation of adenosine triphosphate and pyruvate, and the latter is reduced with nicotinamide-adenine dinucleotide (reduce form) in the presence of lactate dehydrogenase to give nicotinamide-adenine dinucleotide (oxidized form) which is then determined.

10. Method as claimed in claim 1 wherein glycerol-1-phosphate is further reacted with oxygen in the presence of glycerol-1-phosphate oxidase to give dihydroxyacetone phosphate and hydrogen peroxide which is reacted with 4-aminoantipyrine and a phenol or aniline derivative in the presence of peroxidase to form a colored material which is determined.

11. Method as claimed in claim 1 wherein adenosine diphosphate is phosphorylated with phosphoenol pyruvate in the presence of pyruvate kinase to form adenosine triphosphate and pyruvate, the so formed pyruvate is reacted with oxygen and pyruvate oxidase to form acetyl phosphate, carbon dioxide and hydrogen peroxide and the latter is reacted with a phenol or aniline derivatives in the presence of peroxidase to give a colored material which is determined.

12. Reagent for the determination of triglycerides comprising lipase, adenosine triphosphate, glycerokinase, a reagent system for determining glycerol-1-phosphate or adenosine diphosphate and a glycerokinase from *Bacillus stearothermophilis*, with at least one lipase activator selected from the group consisting of polyethylene oxide ester surfactants, polyethylene oxide ether surfactants, bile acid surfactants, alkyl sulphate surfactants, phenol derivatives and aniline derivatives.

13. Reagent as claimed in claim 12 wherein said activator is a polyethylene oxide ester.

14. Reagent as claimed in claim 12 wherein said activator is a polyethylene oxide ether.

15. Reagent as claimed in claim 12 wherein said activator is a bile acid.

16. Reagent as claimed in claim 12 wherein said activator is an alkyl sulphate.

17. Reagent as claimed in claim 12 wherein said activator is a phenol substituted with a substituent selected from the group consisting of carboxyl, sulphonic, hydrogen and nitro.

18. Reagent as claimed in claim 12 wherein said activator is an aniline substituted with a substituent selected from the group consisting of carboxyl, sulphonic, halogen and nitro.

19. Reagent as claimed in claim 12 wherein said activator is a sodium dodecyl phosphate.

20. Reagent as claimed in claim 12 wherein said reagent system for determining adenosine diphosphate comprises phosphoenol pyruvate, pyruvate kinase, nictotinamide-adenine dinucleotide and lactate dehydrogenase.

21. Reagent as claimed in claim 12 wherein said activator is dichlorophenol.

22. Reagent as claimed in claim 12 wherein said activator is sodium cholate and an alkyl aryl polyethylene oxide ester.

23. Reagent as claimed in claim 12 wherein said activator is 2,4-dichlorophenol, isotridecylpolyethylene oxide ether and sodium cholate.

24. Reagent as claimed in claim 12 wherein said system for determining glycerol-1-phosphate comprises glycerol phosphate oxidase, peroxidase and-4-aminoantipyrine.

25. Reagent as claimed in claim 12 comprising
60 to 200 U lipase,
0.4 to 10 U esterase,
0.5 to 10 U glycerokinase from *Bacillus stearothermophilis*,
0.5 to 10 U pyruvate kinase,
2 to 10 U lactate dehydrogenase,
0.25 to 0.7 μMol phosphoenol pyruvate,
0.25 to 0.7 μMol ATP,
0.15 to 0.3 μMol NADH,
0.3 to 0.5 μMol sodium dodecyl sulphate,
4 to 100 μMol MgSO$_4$ and
20 to 100 μMol phosphate buffer (pH 6.8 to 7.5) referred to 1 ml. of reagent solution.

26. Reagent as claimed in claim 12 comprising
0.6 to 10 U esterase,
60 to 300 U lipase, 0.5 to 10 U glycerokinase from *Bacillus stearothermophilis*,
0.5 to 10 U pyruvate kinase,
2 to 10 U lactate dehydrogenase,
0.15 to 3 μMol NADH,
0.25 to 0.7 μMol phosphoenol pyruvate,
0.25 to 0.7 μMol ATP,
1.5 to 4 μMol 2,3-dichlorophenol,
1.5 to 5.0 mg. sodium cholate,
0.8 to 2 μl. octylphenylpolyethylene oxide ester,
150 to 300 μMol MgSO$_4$ and
40 to 100 μMol tris/powdered tartaric acid (pH 7.0 to 7.6) referred to 1 ml. of reagent solution.

27. Reagent as claimed in claim 12 comprising 0.6 to 10 U esterase,
60 to 300 U lipase,
0.5 to 10 U glycerokinase from *Bacillus stearothermophilis*,
2 to 10 U glycerol phosphate oxidase,
0.3 to 1 μMol ATP,
3 to 10 μMol 2,4-dichlorophenol,
1.5 to 5.0 mg. sodium cholate,
1.5 to 10 μl. isotridecylpolyethylene oxide ether,
150 to 300 μMol magnesium sulphate,
40 to 100 Mol buffer (pH 7.5 8.5) referred to 1 ml. of reagent solution.

28. Method of claim 1 wherein, along with lipase, esterase is used for the determination.

* * * * *